United States Patent [19]

Chapman et al.

[11] 4,225,741

[45] Sep. 30, 1980

[54] PARALLEL ALKYLATION REACTIONS UTILIZING PRESSURED VAPOROUS ISOPARAFFIN FOR INDIRECT HEAT EXCHANGE WITH FRACTIONATORS AND/OR HF STRIPPERS

[75] Inventors: Charles C. Chapman; Paul D. Hann, both of Bartlesville, Okla.

[73] Assignee: Phillips Petroleum Company, Bartlesville, Okla.

[21] Appl. No.: 62,663

[22] Filed: Aug. 1, 1979

[51] Int. Cl.$^2$ .............................................. C07C 3/54
[52] U.S. Cl. ..................................... 585/719; 585/723
[58] Field of Search ......................... 585/716, 719, 723

[56] References Cited

U.S. PATENT DOCUMENTS

| | | | |
|---|---|---|---|
| 2,392,962 | 1/1946 | Abrams et al. | 585/723 |
| 2,416,395 | 2/1947 | Kuhn, Jr. | 585/723 |
| 2,536,515 | 1/1951 | Penick | 585/719 |
| 3,158,661 | 11/1964 | Plaster et al. | 585/723 |
| 3,478,125 | 11/1969 | Chapman | 585/723 |
| 3,544,651 | 12/1970 | Chapman | 585/723 |
| 3,763,022 | 10/1973 | Chapman | 585/723 |
| 3,957,901 | 5/1976 | Chapman | 585/719 |

Primary Examiner—George Crasanakis

[57] ABSTRACT

A process is provided for the simultaneous and separate alkylation of an isoparaffin such as isobutane with different olefins, e.g., propylenes and butylenes in different zones with an HF acid catalyst comprising separating the hydrocarbon phase from each of the alkylation effluents, subjecting each hydrocarbon phase to separate HF stripping, fractionating the liquid phases removed from each of the HF stripping zones, pressurizing the vaporous isoparaffin stream recovered from fractionation and utilizing the pressurized vaporous streams for indirect heat exchange with HF strippers and fractionation zones prior to recycling through alkylation.

8 Claims, 1 Drawing Figure

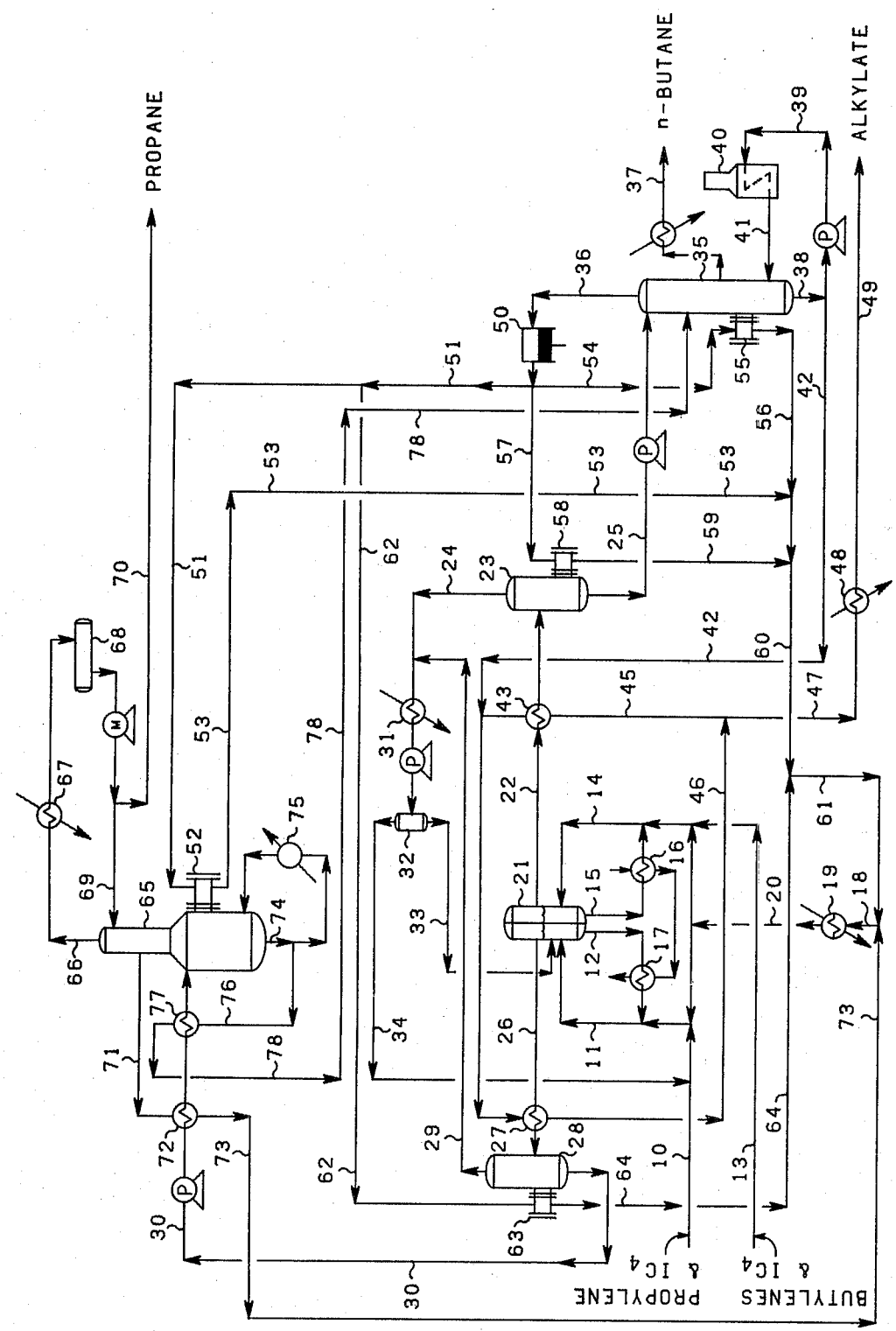

PARALLEL ALKYLATION REACTIONS UTILIZING PRESSURED VAPOROUS ISOPARAFFIN FOR INDIRECT HEAT EXCHANGE WITH FRACTIONATORS AND/OR HF STRIPPERS

BACKGROUND OF THE INVENTION

This invention relates to a process for the alkylation of isoparaffins with two or more different olefins with a liquid acid alkylation catalyst. In accordance with another aspect, this invention relates to a process for the HF alkylation with isoparaffin with different olefins and the recovery of substantially HF-free isoparaffins which can be compressed and utilized as an indirect heat exchange medium with various pieces of separation equipment separating the alkylation effluent. In accordance with a further aspect, this invention relates to a process for simultaneously and separately HF alkylating isobutane with propylene and isobutane with butylene, HF stripping each reaction effluent and then fractionating and recovery of isobutane vapors which are free of HF and which are compressed and used for indirect heat exchange with the HF strippers and fractionation zones. In accordance with a further aspect, this invention relates to the process for separating the reaction effluents formed from isobutane, olefins and hydrofluoric acid catalysts wherein a product stream, free of HF, is recovered and utilized as a heat exchange medium for heating the process equipment thereby minimizing energy requirements for the fractionation and separation equipment.

Accordingly, an object of this invention is to provide an improved process for simultaneously alkylating one or more isoparaffins with at least two different olefins.

Another object of this invention is to provide an improved process for simultaneously and separately alkylating an isoparaffin with two or more olefins and the recovery of the product therefrom.

A further object of this invention is to provide an improved process which effects improved heat exchange advantages over other systems in the recovery of HF alkylation reaction effluents.

Other objects and aspects as well as the several advantages of the invention will become apparent upon consideration of the accompanying disclosure, the drawing and the appended claims.

SUMMARY OF THE INVENTION

In accordance with the invention, a process is provided which comprises alkylating in separate alkylators an isoparaffin with different olefins using a liquid acid alkylation catalyst, separately recovering the different alkylates from the acid catalyst, stripping HF from each of the different alkylates, fractionating each of the HF stripped alkylates to recover a vaporous isoparaffin stream which is free of HF and which is pressurized and used as an indirect heat exchange medium for the separation equipment.

In accordance with one embodiment of the invention, isobutane is HF alkylated with propylene and with butylenes in separate alkylation reaction zones, the reaction effluent from each reaction zone is separated into an acid phase and a hydrocarbon phase, each of the hydrocarbon phases is subjected to HF stripping and the bottoms, free of HF, removed from each stripping subjected to fractionation and isobutane is recovered from the fractionation, is pressurized and then used as indirect heat exchange medium for the HF stripping zones and fractionation zones prior to recycling to each of the alkylation zones.

Further, in accordance with the presently preferred embodiment, propylene and butylenes are simultaneously and separately subjected to HF alkylation with isobutane in different reaction zones. The propylene alkylate is charged to an HF stripper with HF-free bottoms being charged to the depropanizer, operated under HF-free conditions. The butylenes alkylate goes to its HF stripper and the Hf-free bottoms are charged to the isobutane stripper. Overhead HF-hydrocarbon from each HF stripper are combined, cooled, and charged to liquid full separator. HF phase is returned to the propylene alkylation settler; the hydrocarbon is recycled to the propylene alkylation reactor. The isotripper yields normal butane and alkylate plus HF-free isobutane vapor which can now be compressed and used to indirectly heat: (a) interheater on the depropanizer; (b) interheater on the isostripper; and (c) each reboiler on the HF strippers. The now cooler isobutane is further cocled and recycled to both alkylation reactions. Cooling water indirectly first cools the recycle HF on butylenes alkylation and then the recycle HF on the propylene alkylation.

The reaction effluents from the different alkylation zones can be passed to a common alkylate-acid settler which is described in U.S. Pat. No. 3,544,651 or to individual settling zones. The preferred olefins in the process are propylene and butylenes, but any $C_3$-$C_7$ olefins can be used. Isobutane is preferred as the isoparaffin but $C_4$-$C_8$ isoparaffins can be used. The specific reaction conditions employed are conventional and well-known in the art. The mol ratio of isoparaffin to olefin is usually maintained in the range of 4:1 to 20:1. The volume ratio of acid to hydrocarbon feed can range from 0.5:1 to 6:1. The alkylation temperature can vary from about 40° F.–200° F.; however, when alkylating isobutane with butylene a reaction temperature in the range of about 60° F.–95° F. is preferred and when alkylating isobutane with propylene a temperature in the range of approximately 100° F.–125° F. is preferred.

A better understanding of the invention will be obtained by reference to the accompanying schematic drawing showing an arrangement with apparatus illustrating the preferred embodiment of the invention.

Referring to the drawing, propylene and isobutane feed in line 10 are charged to riser-reactor 11 to HF alkylate isobutane with propylene in the presence of HF acid catalyst. Recycle HF acid catalyst in line 12 is combined with feed propylene and isobutane along with recycled isobutane at the entrance to reaction zone 11. Butylenes and isobutane feed in line 13 are charged to riser-reactor 14 to HF alkylate isobutane with butylene. HF acid catalyst recycled by line 15 after cooling in heat exchanger 16 is mixed with incoming butylenes and isobutane feed at the entrance of reactor 14. Similarly, HF acid recycle in line 12 is cooled in cooler 17 prior to introduction into reactor 11.

Cooling of the recycled HF acid in lines 12 and 15 is effected by water cooling the butylenes unit in heat exchanger 16 before cooling the propylenes acid in heat exchanger 17 since propylene alkylation can be operated at a higher temperature than butylenes alkylation without octane sacrifice.

Recycle isobutane in line 18 is cooled in heat exchanger 19 and passed by way of line 20 for introduction into riser-reactors 11 and 14 along with feed olefins to these units.

As shown in the drawing, a common alkylate acid settler unit 21 is provided such as described in U.S. Pat. No. 3,544,651. The butylenes alkylate from divided settler 21 is removed at line 22 and charged to HF stripper 23 wherein the butylenes alkylate is subjected to stripping conditions sufficient to remove overhead HF and low boiling hydrocarbons by line 24 and the bottom hydrocarbon fraction substantially free of HF by way of line 25.

The hydrocarbon fraction separated from settler 21 from the propylene alkylation is removed by line 26 and passed through heat exchanger 27 and introduced into HF stripper 28 wherein the propylenes alkylate is subjected to conditions sufficient to remove overhead HF and low boiling hydrocarbons by line 29 and bottoms by line 30.

The HF-containing overhead in line 29 removed from stripper 28 and in line 24 removed from stripper 23 are combined and cooled in heat exchanger 31 and passed to liquid full separator 32. A condensed phase separated HF is removed from separator 32 by line 33 and returned to unit 21 through the propylene alkylation settler side of the settler. The propane-containing hydrocarbon removed from separator 32 by line 34 is passed through the propylene alkylation system and introduced into feed line 10.

The hydrocarbon phase removed from the bottom of HF stripper 31 by line 25 is passed to isostripper 35 wherein the HF-free butylene alkylate is subjected to fractionation conditions sufficient to remove substantially HF-free isobutane overhead by line 36, normal butane as a side stream by line 37 and alkylate as bottoms by way of line 38. A portion of the alkylates bottom is recycled to isostripper 35 by way of line 39, fired reboiler 40 and line 41.

The remainder of the alkylate removed from isostripper 35 is passed by line 42 through heat exchangers 43 and 27 to indirectly heat hydrocarbon streams 22 and 26, respectively, prior to these streams being charged to HF strippers 23 and 28, respectively. The cooled alkylate in lines 45 and 46 are combined in line 47, further cooled in heat exchanger 48 and removed from the system as product by way of line 49.

Isobutane vapor removed from overhead from isostripper 35 by line 36 is passed to compressor 50 and then used as indirect heat exchange as described in more detail hereinbelow and ultimately recycled to both alkylation steps 11 and 14. Compressed isobutane vapors removed from compressor 50 are passed by way of line 51 through heater 52 and line 53 for combination with heat exchanged isobutane vapors passed in line 54 through heat exchanger 55 and thence in line 56. Another portion of the compressed isobutane vapors is passed through line 57, heat exchanger 58 and line 59 for combining with cooled isobutane in line 56. The combined stream in line 60 is passed by way of line 61 and introduced into line 18 for passage to the alkylation reactors 11 and 14.

Another portion of the isobutane vapors in line 51 is passed by line 62 through heat exchanger 63, line 64 and combined with cooled isobutane in line 60 for recycle to alkylation reactors.

The bottoms from HF stripper 28 in line 30 is passed to depropanizer 65 wherein the propylene alkylate is subjected to fractionation conditions sufficient to remove propane overhead in line 66 which is condensed in cooler 67, passed to accumulator 68 and a portion of the condensate returned by line 69 to depropanizer 65 and the remainder removed as product by way of line 70. An isobutane side stream is removed from depropanizer 65 by line 71 and heat exchanged with feed in line 30 in heat exchanger 72 then passed by line 73 for recycle to alkylation units 11 and 14. A portion of the propylene alkylate bottoms is removed from depropanizer 65 by line 74, sent through reboiler 75 and returned to depropanizer 65. The remainder is taken by line 76, heat exchanged with feed in heat exchanger 77 and passed by line 78 as part of the feed to isostripper 35.

HF stripper 23 which is utilized to strip HF from a butylene alkylate stream is operated under conditions, temperature and pressure such that HF vapor and lighter hydrocarbon vapors are taken overhead and a liquid hydrocarbon stream free of HF as bottoms. Usually the temperature in the upper portion of the stripper will be in the range of about 110° F. to about 130° F., the bottom temperature in the range of about 150° F. to about 180° F., and a pressure of about 100 psig to about 150 psig.

The isostripper 35 will be operated at conditions of relatively low pressure to separate isobutane vapor overhead and alkylate liquid as product with normal butane vapor as a side stream. This would usually require a top temperature in the range of about 130° F. to about 150° F., with a bottom temperature in the range of about 310° F. to about 340° F. and a pressure in the range of about 100 psig to about 140 psig.

Depropanizer 65 is operated under conditions to take propane vapor overhead and isobutane liquid as bottoms usually at a top temperature of about 115° F. to about 140° F. and a bottom temperature of about 190° F. to about 235° F. and a pressure in the range of about 220 psig to about 275 psig will be used. Depropanizer 65 is operated so as to take isobutane as a side stream.

HF stripper 28 which is utilized to strip HF from the propylene alkylate removed from alkylation zone 11 is operated under conditions to take overhead as vapor substantially all of the HF remaining in the feed to the stripper and propylene alkylate as bottoms which can contain some propane and isobutane and will be operated under a top temperature in the range of about 105° F. to about 140° F., a bottom temperature in the range of about 150° F. to about 190° F. and a pressure in the range of about 110 psig to about 140 psig.

SPECIFIC EXAMPLE

Using the process of the invention shown in the drawing, the following flow rates and the following operating conditions for specific components of the system were calculated.

| TYPICAL OPERATION (Calculated) | |
|---|---|
| I. Operating Conditions: | |
| HF Alkylations: | |
| Butylenes Alkylation (14): | |
| Pressure, psia | 165 |
| Temperature, °F. | 90 |
| IC$_4$/Olefins Mol. Ratio | 11:1 |
| H/C to HF Vol. Ratio | 4:1 |
| Residence Time, Min. | 0.5 |
| Propylene Alkylation (11): | |
| Pressure, psia | 165 |
| Temperature, °F. | 100 |
| IC$_4$/Olefins Mol. Ratio | 11:1 |
| H/C to HF Vol. Ratio | 4:1 |

-continued

TYPICAL OPERATION
(Calculated)

| | |
|---|---|
| Residence Time, Min. | 0.5 |
| HF Stripper (23) (Butylenes Alkylate): | |
| Pressure, psia | 125 |
| Top Temperature, °F. | 120 |
| Bottom Temperature, °F. | 160 |
| HF Stripper (28) (Propylene Alkylate): | |
| Pressure, psia | 125 |
| Top Temperature, °F. | 110 |
| Bottom Temperature, °F. | 160 |
| Depropanizer (65): | |
| Pressure, psia | 265 |
| Top Temperature, °F. | 130 |
| Bottom Temperature, °F. | 220 |
| Isostripper (35): | |
| Pressure, psia | 130 |
| Top Temperature, °F. | 140 |
| Bottom Temperature, °F. | 325 |

II. Flows and Compositions:

| | | |
|---|---|---|
| (11) Fresh Feed to Propylene Alkylation B/H | | 100 |
| Composition | Vol. % | |
| Propane | 15 | |
| Propylene | 35 | |
| Isobutane | 45 | |
| n-Butane | 5 | |
| (14) Fresh Feed to Butylenes Alkylation B/H | | 100 |
| Composition | Vol. % | |
| Butylenes | 46 | |
| Isobutane | 51 | |
| n-Butane | 3 | |
| (36) Isobutane Vapor (140° F.) (a) (B/H) | | 545 |
| (Vol. % iC$_4$ 90) | | |
| (Wt. % HF nil) | | |
| (73) Isobutane, B/H | | 267 |
| (Vol. % iC$_4$ 90) | | |
| (Wt. % HF nil) | | |
| (22) Hydrocarbon to HF Stripper (23), B/H | | 583 |
| (Not including HF in numeral) | | |
| (26) Hydrocarbon to HF Stripper (28), B/H | | 475 |
| (Not including HF in numeral) | | |
| (24) Vapor from (23) (a) (B/H) | | 50 |
| (Numeral does not include HF) | | |
| (25) Liquid from (23), B/H | | 533 |
| (HF-free) | | |
| (29) Vapor from (28) (a) (B/H) | | 35 |
| (Numeral does not include HF) | | |
| (30) Liquid from (28), B/H (HF-free) | | 440 |
| (70) Propane Yield, B/H | | 15 |
| (33) HF from (32), B/H | | 12 |
| (34) Hydrocarbon from (32), B/H | | 85 |
| (Contains soluble HF) | | |
| (Not included in numeral) | | |
| (49) Alkylate Yield, B/H | | 140 |
| (Estimated RON Clear 93) | | |
| (37) Normal Butane Yield, B/H | | 8 |
| Split of Isobutane Vapor (36) | | |
| Compressed to 300 psig; 215° F.; | | |
| | Vol. % | |
| To 51 | 30 | |
| To 57 | 10 | |
| To 54 | 50 | |
| To 62 | 10 | |
| Which use of (36) gives a savings in Btu/hr of 20 × 10$^6$. | | |

(a) (B/H) Actually vapor, reported as B/H liquid.

We claim:

1. An alkylation process which comprises:
 (a) reacting in a first reaction zone (A), isobutane with propylene in the presence of HF acid under conditions which form alkylate;
 (b) separating the alkylation reaction effluent from (a) into a liquid HF acid phase and a liquid hydrocarbon phase containing residual HF acid;
 (c) passing said liquid hydrocarbon phase, separated in (b) to the first HF stripping zone and subjecting same to stripping conditions to remove HF and light hydrocarbons overhead and a hydrocarbon stream substantially free of HF as bottoms;
 (d) fractionating said bottoms separated in (c) into a propane overhead stream and isobutane side stream and a first propylene alkylate bottoms stream;
 (e) reacting in a second reaction zone (B) isobutane with butylenes in the presence of HF acid under conditions which form alkylate;
 (f) separating the alkylation effluent from (d) into a liquid HF acid phase and a liquid hydrocarbon phase containing residual HF acid;
 (g) passing said liquid hydrocarbon phase separated in (f) to a second HF stripping zone and subjecting same to stripping conditions to remove HF, light hydrocarbons overhead and a hydrocarbon stream substantially free of HF as bottoms;
 (h) fractionating said bottoms separated in (g) into an isobutane overhead stream, a butane side stream and a butylenes alkylate bottoms stream;
 (i) pressurizing said vaporous overhead isobutane stream separated from (h) and
 (j) passing said pressurized stream of (i) into a heat exchange relationship with at least one of;
   (1) the lower portion of said fractionation zone in (d) and (h) and
   (2) the lower portion of said HF first and second stripping zones in (c) and (g).

2. A process according to claim 1 wherein said presurized stream of isobutane separated in step (i) is passed in indirect heat exchange relationship with all of the units of (1) and (2) and after indirect heat exchange, the cooled isobutane is recycled to reaction zones (a) and (b).

3. A process according to claim 1 wherein the propylene alkylate bottoms stream in (d) is passed as part of the feed to fractionation zone in (h).

4. A process according to claim 1 wherein isobutane is removed as a side stream from fractionation zone in (d) and recycled to reaction zones (A) and (B).

5. A process according to claim 1 wherein the butylene alkylate bottoms separated from (h) is used to indirectly heat exchange the effluents from reaction zones (A) and (B) prior to introduction into HF stripping zones in (c) and (g).

6. In a process for simultaneously and separately HF alkylating isobutane with propylene in a first reaction zone and isobutane with butylenes in a second reaction zone and separating the reaction effluents from each reaction zone into an acid phase and a hydrocarbon phase, the improvement which comprises:
 (a) stripping HF from the hydrocarbon phase separated from the effluent of said first reaction zone and passing bottoms substantially free of HF to a depropanizing zone for recovery of propane overhead and propylene alkylate as bottoms;
 (b) stripping HF from the hydrocarbon phase separated from the reaction effluent of said second reaction zone and passing the bottoms remaining substantially free of HF to an isostripper, recover HF-free isobutane vapors overhead, a butane side stream and butylene alkylate bottoms;
 (c) pressurize said isobutane vaporous overhead obtained in (b);
 (d) passing the pressurized isobutane of (c) in indirect heat exchange with the lower portion of said depropanizer, said isostripper, each of said HF stripping zones of (a) and (b); and (e) recycling cold isobutane after heat exchange in (d) to the first and second reaction zones.

7. A process according to claim 6 wherein the bottoms from said depropanizer is passed to said isostripper as part of the feed.

8. A process according to claim 6 wherein isobutane is separated from said depropanizer as a side stream and returned to said first and second reaction zones.

* * * * *